(12) United States Patent
Bao et al.

(10) Patent No.: US 11,860,048 B2
(45) Date of Patent: Jan. 2, 2024

(54) CAPACITIVE AND TACTILE SENSORS AND RELATED SENSING METHODS

(71) Applicant: The Board of Trustees of the Leland Stanford Junior University, Stanford, CA (US)

(72) Inventors: Zhenan Bao, Stanford, CA (US); Mark R. Cutkosky, Palo Alto, CA (US); Jooyeun Ham, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 907 days.

(21) Appl. No.: 16/629,380

(22) PCT Filed: Jul. 10, 2018

(86) PCT No.: PCT/US2018/041476
§ 371 (c)(1),
(2) Date: Jan. 8, 2020

(87) PCT Pub. No.: WO2019/014243
PCT Pub. Date: Jan. 17, 2019

(65) Prior Publication Data
US 2020/0141818 A1    May 7, 2020

Related U.S. Application Data

(60) Provisional application No. 62/530,667, filed on Jul. 10, 2017.

(51) Int. Cl.
*G01L 1/14* (2006.01)
*B25J 13/08* (2006.01)
(Continued)

(52) U.S. Cl.
CPC .............. *G01L 1/144* (2013.01); *B25J 13/081* (2013.01); *G01L 1/22* (2013.01); *G01L 9/12* (2013.01);
(Continued)

(58) Field of Classification Search
CPC ... G01L 1/144; G01L 1/22; G01L 9/12; G01L 19/0092; B25J 13/081; H01G 4/012;
(Continued)

(56) References Cited

U.S. PATENT DOCUMENTS 5,030,931 A    7/1991 Brooks et al.
7,343,813 B1 *  3/2008 Harrington ............. G01L 1/146
                                                  73/780
(Continued)

FOREIGN PATENT DOCUMENTS

CN    103250218 A    8/2013
WO    2012/034122 A1    3/2012

OTHER PUBLICATIONS

USPTO. International Search Report and Written Opinion dated Sep. 25, 2018, for parent PCT Application No. PCT/US2018/041476, 10 pages.
(Continued)

*Primary Examiner* — Jonathan M Dunlap
(74) *Attorney, Agent, or Firm* — Crawford Maunu PLLC

(57) ABSTRACT

Aspects of various embodiments are directed to sensor apparatuses and methods thereof. An example sensor apparatus includes a capacitor and sensor circuitry. The capacitor includes a first substrate having a first electrode, a second substrate having a second electrode, and a dielectric layer. The dielectric layer has a plurality of dielectric structures arranged in a pattern, the first and second electrode being separated by the dielectric layer and arranged with an overlapping area with respect to one another. The sensor
(Continued)

circuitry is coupled to the capacitor and configured and arranged to detect normal and shear forces applied to the sensor apparatus based on changes in capacitance derived from changes in at least one of a distance between first and second electrodes and the overlapping area of the first and second electrodes.

23 Claims, 5 Drawing Sheets

(51) Int. Cl.
  *G01L 1/22*    (2006.01)
  *G01L 9/12*    (2006.01)
  *G01L 19/00*   (2006.01)
  *H01G 4/012*   (2006.01)
  *H01G 4/33*    (2006.01)
  *H03K 17/96*   (2006.01)
  *A61B 5/00*    (2006.01)

(52) U.S. Cl.
  CPC ......... *G01L 19/0092* (2013.01); *H01G 4/012* (2013.01); *H01G 4/33* (2013.01); *H03K 17/962* (2013.01); *A61B 5/6843* (2013.01); *A61B 2562/0247* (2013.01); *A61B 2562/0261* (2013.01); *H03K 2217/96062* (2013.01); *H03K 2217/960755* (2013.01)

(58) Field of Classification Search
  CPC ................... H01G 4/33; H03K 17/962; H03K 2217/96062; H03K 2217/960755; A61B 5/6843; A61B 2562/0247; A61B 2562/0261
  See application file for complete search history.

(56) References Cited

U.S. PATENT DOCUMENTS

| | | | |
|---|---|---|---|
| 8,047,075 B2 | 11/2011 | Nasiri et al. | |
| 8,181,540 B2 | 5/2012 | Loeb et al. | |
| 9,003,898 B2* | 4/2015 | Moon | G01L 5/165 345/173 |
| 9,700,258 B2* | 7/2017 | Jiang | G01L 1/127 |
| 9,823,141 B2* | 11/2017 | Li | G01L 1/146 |
| 10,113,925 B2* | 10/2018 | Lai | G01L 1/14 |
| 10,267,690 B2* | 4/2019 | Wu | G01L 5/165 |
| 10,635,219 B2* | 4/2020 | Chou | G06F 3/0446 |
| 11,137,297 B2* | 10/2021 | Sawada | G01L 1/146 |
| 2006/0016275 A1 | 1/2006 | Gravesen et al. | |
| 2006/0079354 A1 | 4/2006 | Ammer | |
| 2009/0160461 A1 | 6/2009 | Zangl | |
| 2010/0282310 A1 | 11/2010 | Tsoi | |
| 2012/0105361 A1 | 5/2012 | Kremin | |
| 2013/0093437 A1* | 4/2013 | Koo | G01R 27/2605 324/660 |
| 2014/0109695 A1 | 4/2014 | Lipomi et al. | |
| 2014/0150572 A1* | 6/2014 | Lim | G06F 3/0338 73/862.626 |
| 2014/0174204 A1* | 6/2014 | Chen | G01L 5/226 156/182 |
| 2014/0298921 A1 | 10/2014 | Surapaneni et al. | |
| 2014/0350348 A1 | 11/2014 | Tee et al. | |
| 2016/0015311 A1* | 1/2016 | Jiang | G01L 5/164 600/592 |
| 2016/0041652 A1 | 2/2016 | Bao et al. | |
| 2016/0054813 A1 | 2/2016 | Schediwy et al. | |
| 2016/0256070 A1 | 9/2016 | Murphy et al. | |
| 2016/0363489 A1* | 12/2016 | Li | G01L 1/146 |
| 2017/0045976 A1 | 2/2017 | Bushnell et al. | |
| 2017/0176266 A1 | 6/2017 | Mathieu et al. | |
| 2017/0248482 A1 | 8/2017 | Nishioki et al. | |
| 2018/0225990 A1* | 8/2018 | Jiang | G09B 23/28 |

OTHER PUBLICATIONS

CNIPA. Notice of First Office Action dated Jun. 2, 2021, for related Chinese Patent Application No. 201880058370.7, 7 pages, with English translation.
AD7147: CapTouch Programmable Controller forSingle-Electrode Capacitance Sensors, Rev. E. Analog Devices, Inc. (2007-2015), 70 pgs. www.analog.com/media/en/technical-documentation/data-sheets/AD7147.
Lipomi, D., Vosgueritchian, M., Tee, BK. et al. Skin-like pressure and strain sensors based on transparent elastic films of carbon nanotubes. Nature Nanotech 6, 788-792 (2011).
Hanna Yousef, Mehdi Boukallel, Kaspar Althoefer, Tactile sensing for dexterous in-hand manipulation in robotics—A review. Sensors and Actuators A: Physical, vol. 167, Issue 2, 2011, pp. 171-187.
Heyneman B, Cutkosky MR. Slip classification for dynamic tactile array sensors. The International Journal of Robotics Research. 2016; 35(4): 404-421.
Kappassov, Y. Khassanov, A. Saudabayev, A. Shintemirov and H. A. Varol, "Semi-anthropomorphic 3D printed multigrasp hand for industrial and service robots," 2013 IEEE International Conference on Mechatronics and Automation, 2013, pp. 1697-1702.
Benjamin C.-K. Tee et al. A skin-inspired organic digital mechanoreceptor. Science, vol. 350, Issue 6258, (Oct. 16, 2015) pp. 313-316.
J. Ulmen and M. R. Cutkosky, "A robust, low-cost and low-noise artificial skin for human-friendly robots", IEEE International Conference on Robotics and Automation, (2010), pp. 4836-4841.
A. Schmitz, P. Maiolino, M. Maggiali, L. Natale, G. Cannata and G. Metta, "Methods and Technologies for the Implementation of Large-Scale Robot Tactile Sensors," in IEEE Transactions on Robotics, vol. 27, No. 3, pp. 389-400.
Rui Li, Edward H. Adelson. Sensing and Recognizing Surface Textures Using a GelSight Sensor. Proceedings of the IEEE Conference on Computer Vision and Pattern Recognition (CVPR), 2013, pp. 1241-1247.
H. Xie, A. Jiang, H. A. Wurdemann, H. Liu, L. D. Seneviratne and K. Althoefer, "Magnetic Resonance-Compatible Tactile Force Sensor Using Fiber Optics and Vision Sensor," in IEEE Sensors Journal, vol. 14, No. 3, pp. 829-838, Mar. 2014.
B. Choi, H. R. Choi, and S. Kang, "Development of tactile sensor for detecting contact force and slip", IEEE/RSJ International Conference on Intelligent Robots and Systems, (2005), pp. 2638-2643 (Korean language).
J. A. Fishel and G. E. Loeb, "Sensing tactile microvibrations with the biotac comparison with human sensitivity", IEEE RAS EMBS International Conference on Biomedical Robotics and Biomechatronics, (2012), pp. 1122-1127.
TakkTile. "TakkTile for Robotiq gripper." (retrieve Aug. 6, 2021), 2 pgs. www.takktile.com.
A. Drimus, G. Kootstra, A. Bilberg, D. Kragic, "Design of a flexible tactile sensor for classification of rigid and deformable objects", Robotics and Autonomous Systems, 62 (2014), pp. 3-15 (Abstract Only).
R. Koiva, M. Zenker, C. Schurmann, R. Haschke, H. Ritter, "A highly sensitive 3D-shaped tactile sensor", IEEE/ASME International Conference on Advanced Intelligent Mechatronics, (2013), pp. 1084-1089 (Abstract Only).
D. Göger, N. Gorges, H. Worn, "Tactile sensing for an anthropomorphic robotic hand: Hardware and signal processing", IEEE International Conference on Robotics and Automation, (2009), pp. 895-901 (Abstract Only).
T. Zhang, H. Liu, L. Jiang, S. Fan, J. Yang, "Development of a flexible 3-d tactile sensor system for anthropomorphic artificial hand", IEEE Sensors, 13 (2013), pp. 510-518 (Abstract Only).
The Examiner is respectfully referred to copending patent prosecution of the common Applicant, U.S. Appl. No. 17/255,704, filed Dec. 23, 2020 (No Attachment).
Honeywell, Bridge pressure sensor, www.sccatalog.honeywell.com (No Attachment).

* cited by examiner

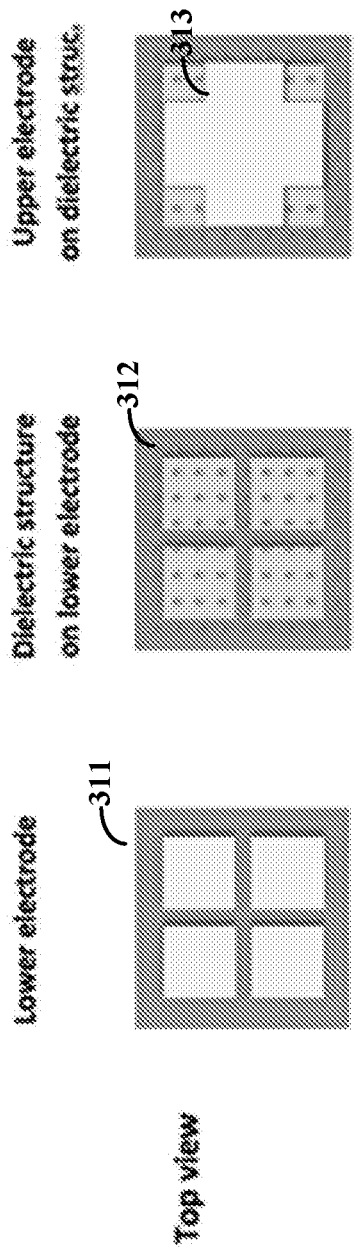
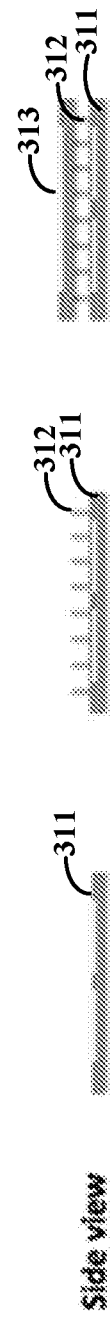
FIG. 3A
FIG. 3B

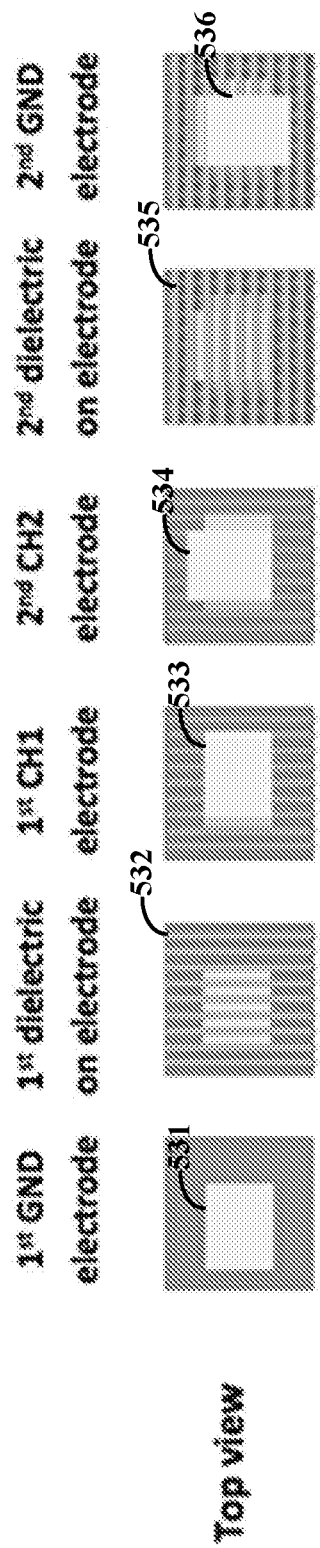
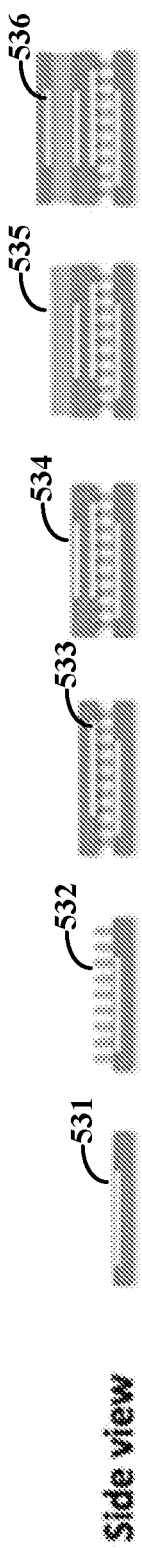
FIG. 5A
FIG. 5B

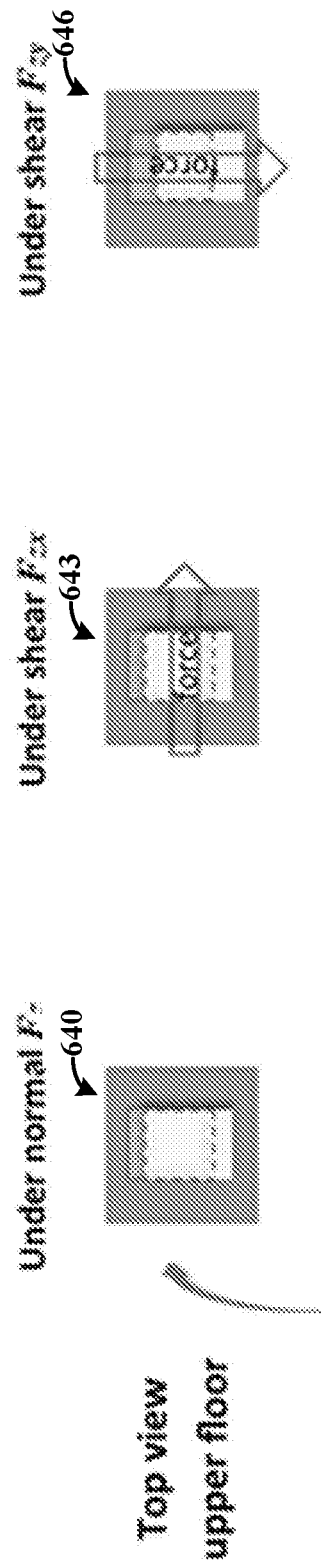
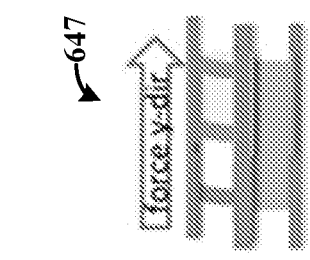
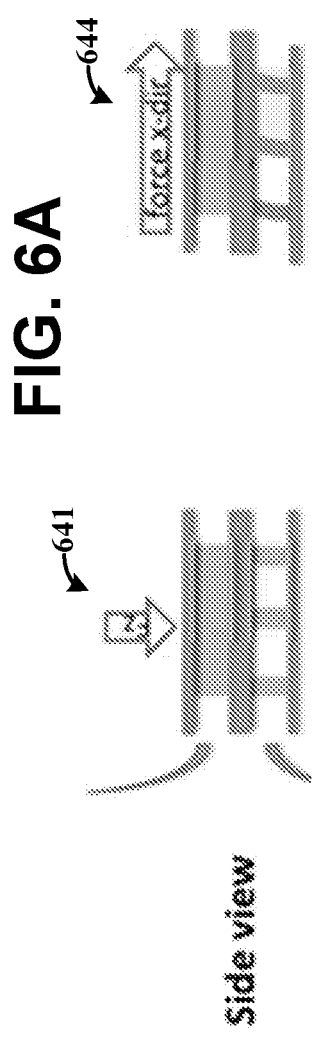
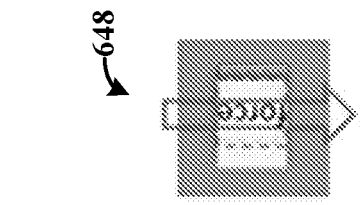
FIG. 6A  FIG. 6B  FIG. 6C

CAPACITIVE AND TACTILE SENSORS AND RELATED SENSING METHODS

OVERVIEW

Human or other animal skin provides a remarkable network of sensitive diverse sensors that provide sensitive pressure and vibration sensing. Skin can transduce environmental stimuli into physiological signals, which are then interpreted by the brain. Various force sensors and devices may attempt to mimic properties of human or animal skin to provide a variety of features.

The above issues as well as others have presented challenges to force sensors for a variety of applications.

SUMMARY

Aspects of various embodiments are directed to capacitive and/or tactile sensors and related sensing methods for sensing static and dynamic forces, and for defining a magnitude and direction of the static and dynamic forces.

In the following discussion, various implementations and applications are disclosed to provide an understanding of the instant disclosure by way of non-limiting example embodiments.

In certain example embodiments, aspects of the present disclosure involve sensor apparatuses specially configured to detect certain forces. For example, the sensor apparatus can be used to classify forces in a three-dimensional axis thereby effectively defining both the magnitude of the force and the direction of the force. These and other aspects employ the sensor circuitry configured to detect both static and dynamic forces and formed of flexible substrates for applications on curved surfaces, such as human skin, consistent with one more of the below-described embodiments and/or mechanisms.

More specific example embodiments are directed to methods and/or apparatuses comprising and/or involving use of a sensor apparatus to sense and detect a magnitude and direction of forces applied to the sensor circuitry in two, three, or more dimensions. The sensor circuitry is configured in a manner to: measure forces applied to the sensor apparatus based on changes in capacitance derived from changes in distance between electrode pairs of a capacitor of the sensor apparatus and/or changes in overlapping areas of the electrode pairs, and/or is formed using flexible substrates, such that the sensor apparatus can be applied to a variety of surfaces including skin and other edges or curved surfaces.

In specific aspects, the sensor apparatus includes a first substrate having at least one electrode and a second substrate having at least one electrode separated by a dielectric layer having a plurality of dielectric structures arranged in a pattern. The first substrate can include four electrodes arranged in a pattern, and the second substrate can include a cross-shaped electrode. Further, the dielectric layer can include a plurality of circular pillars having gaps between and formed of a dielectric material that is arranged between the first and second substrates.

The sensor circuitry can sense and define a magnitude of normal and shear forces by measuring changes in capacitance derived from changes in a gap distance between an electrode of a first substrate of the sensor apparatus and another electrode of a second substrate, the first and second substrates being separated by a dielectric layer. For example, the sensor circuitry can be used to distinguish between shear and normal forces by obtaining a capacitance value from the electrode pairs and comparing the same. In addition, the sensor circuitry can be used to distinguish between torsion and diagonal shear forces by monitoring changes in a capacitance value from the cross-shaped electrode, wherein a torsion force results in capacitance changes in the quadratic and diagonal shear force results in linear capacitance changes.

In a number of related aspects, the sensor circuitry of the sensor apparatus includes at least one capacitance-to-digital converter circuitry that connects the four electrodes of the first substrate to an input channel of the capacitance-to-digital converter circuitry. The sensor circuitry can measure capacitance at a sampling rate using the capacitance-to-digital converter circuitry and connected processing circuitry.

In other specific aspects, the sensor apparatus includes three substrates. The first substrate includes one electrode, the second substrate includes two electrodes, and the third substrate includes one electrode. A first dielectric layer is arranged between the first and second substrates and a second dielectric layer is arranged between the second and third substrates. The first and second dielectric layers include a plurality of rectangular-shaped dielectric structures having gaps between. Further, the rectangular-shaped dielectric structures of the first dielectric layer are arranged perpendicularly with respect to the rectangular-shaped dielectric structures of the second dielectric layer.

Although embodiments are not so limited, and in various aspects, the dielectric layer includes a plurality of structures formed of a dielectric material and having a shape and dimensions targeted for force range and/or sensitivity of the sensor circuitry. The electrodes can be formed of a variety of different materials such as metal, carbon nanomaterial, metal nanowires, and conductive polymers and the dielectric layer can be formed of a variety of polymers.

A number of aspects are directed to methods of forming one or more of the above described sensor apparatuses. An example method includes printing electrode patterns on flexible substrates, such as by using metal deposition and laser ablation, and building a dielectric layer on a first of the flexible substrates. The dielectric layer, as built on the first flexible substrate by chemical bond, is then bonded to a second of the flexible substrates using plasma treatment, and, optionally, the process is repeated for additional layers. In specific aspects, building the dielectric layers includes forming a mold using photolithography, spin-casting a dielectric (e.g., elastomeric) material, such as Polydimethylsiloxane (PDMS), onto the mold and curing the dielectric material in the mold under a patterned electrode, as patterned on the flexible substrate to bond the dielectric material to the pattern electrode.

In various specific aspects, the above-described sensor apparatus is formed as part of another apparatus, such as a robotic or prosthetic apparatus. As a specific example, the sensor apparatus can be part of a robotic hand. When applied in a robotic hand, the sensor apparatus can be used to detect slip of an object being held or touched by the robotic hand. In related specific aspects, the sensor apparatus is formed as part of another apparatus having a plurality of different types of sensors including the sensor apparatus, pressure sensor circuitry, strain sensor circuitry, and/or temperature sensor circuitry, among other types of sensors. The apparatus can further include a wireless communication circuit for wirelessly communicating signals from the sensor circuitry. In some related aspects, the apparatus includes one or more of the electrodes used as a part of a transducer circuit and further including a passively or inductively powered circuit configured to provide power to at least the sensor circuitry of the apparatus. The apparatus can further include a computer (e.g., CPU and/or microcontroller) to provide or assess the forces based on signals provided from the sensor circuitry such as the logic circuitry (e.g., the processor/CPU of FIG. 1 of Appendix A in the underlying provisional application, which is connected to one of the opposing electrodes on either side of the dielectric layer and is configured to use the indication of pressure to carry out data processing tasks, such as for determining pressure characteristics and/or generating an output such as a control signal that is based upon detected pressure).

The above discussion/summary is not intended to describe each embodiment or every implementation of the present disclosure. The figures and detailed description (and including the disclosure in Appendixes A-B that were filed in the underlying provisional application and fully incorporated herein) that follow also exemplify various embodiments.

BRIEF DESCRIPTION OF FIGURES

Various example embodiments may be more completely understood in consideration of the following detailed description in connection with the accompanying drawings, in which:

FIGS. 3A-3B show an example composition of the sensor apparatus as illustrated by FIG. 1, consistent with embodiments of the present disclosure;

FIGS. 5A-5B show an example composition of the sensor apparatus y as illustrated by FIG. 2, consistent with embodiments of the present disclosure; and FIGS. 6A-6C show an example of sensor apparatus under different forces, consistent with embodiments of the present disclosure.

Figure 1:
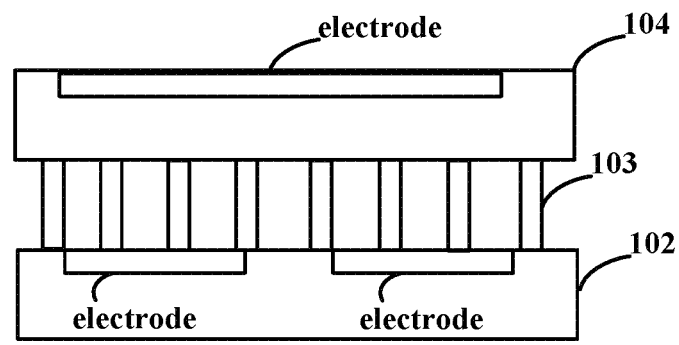
FIG. 1 shows an example sensor apparatus, consistent with embodiments of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses including, and methods involving use of, user-worn force sensor circuitry that senses forces applied thereto and that defines both the magnitude and direction of the force. In certain implementations, aspects of the present disclosure have been shown to be beneficial when used in the context of a skin-like tactile sensor for robotic or prosthetic application, such as robotic hands, but it will be appreciated that the instant disclosure is not necessarily so limited. Various aspects may be appreciated through the following discussion of non-limiting examples which use exemplary contexts.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element. Also, although aspects and features may in some cases be described in individual figures, it will be appreciated that features from one figure or embodiment can be combined with features of another figure or embodiment even though the combination is not explicitly shown or explicitly described as a combination.

Particular example embodiments are directed to a sensor apparatus (e.g., sensory circuitry) that can capacitively detect static and dynamic tactile forces in multiple dimensions (e.g., a three-dimensional axis and in some instances, in two dimensions), and distinguish the forces in the three-dimensional axis. The sensor apparatus can be used to both define a magnitude and direction of the forces based on a design of the dielectric structures and the electrodes of a capacitor of the sensor circuitry. The sensor apparatus can include a capacitor formed of electrode pairs separated by a dielectric layer and sensor circuitry. The dielectric layer can include a plurality of dielectric structures that are shaped to set a sensitivity and force range for the sensor circuitry. The electrodes can be formed on flexible substrates, such that in various implementations, the sensory apparatus can be used in robotics, prosthetic and/or other applications that include surfaces that are curved or have edges. The sensor apparatus can be used in robotics and/or prosthetics to recognize a variety of forces, including both pressure and compression contact (e.g., a normal contact) and a shear slip. In many applications, a force applied on human skin is a combination of normal and two-plane shear forces referring to the skin. For example, the sensor circuitry coupled to the capacitor can be used to classify the force modal and directions, and can be flexible to allow for coverage of the robot's surfaces such as edges or curved ones.

The human skin, including mechanoreceptors, can be indispensable for dexterous activities: detection and reaction to contact by external agents, manipulation of contact location and force control, and exploration of surface texture and local features. In accordance with various embodiments, a sensor apparatus is implemented in robotic and/or prosthetic apparatuses and used to accomplish dexterous activities using sensing information and interaction of the robotic/prosthetic with the environment, like a human. The tactile sensor apparatus, in accordance with various embodiments, can be implemented in robotics and/or prosthetics to provide dexterous activity by providing digital data that matches mechanical stimulations on surface of interaction. In one particular experimental embodiment, the sensor circuitry of the sensor apparatus can exhibit or meet a variety of criteria including, for example, a spatial resolution of 1 mm-5 mm (e.g., 1 mm in finger tips, 5 mm in the palm of the hand, and less than 4 mm for two-point discrimination for an example robotic application), a response time of 1 ms (or less), a force sensitivity of 0.01-10N, and can be flexible. Compare, for example, to known aspects of such forces in robotic/prosthetic applications such as published in Robotics and Autonomous Systems, Z. Kappassov et al. (2015), as reproduced in pertinent part below to exemplify related spatial resolutions and discrimination, response times, ranges, and force sensitivities.

| Cap. Tactile Sensor | Robot Hand | # Tactiles | Res./Sens./ Range | Rate |
|---|---|---|---|---|
| ICub sensor | iCub Humanoid robot | 12 per tip, 48-palm | 7 mm/7 mN/ 150 kPa | 25-250 Hz |
| PPS sensors | PR2 robot grippers | 22 | 4 mm/6.25 mN/ 7 kPa | 24.4 Hz |
| PPS RoboTouch | Allegro robotic hand | 24 | 5 mm/6.25 mN/ 7 kPa | 30-100 Hz |
| Dynamic sensor | Robotiq gripper | 132 | 2 mm/6 mN/15 N (28 kPa) | 300 Hz |
| Combined sensor | Parallel jaw gripper | 50 | 2 mm/10 mN/ 10 N (50 kPa) | 35 kHz |
| PPS RoboTouch | Barrett hand | 120 per finger | 5 mm/6.25 mN/ 7 kPa | 30-100 Hz |

For example, in various specific embodiments the sensor apparatus and/or a plurality of sensor circuits are placed on surfaces of a robot and/or part of a robot that approximates the size of a human hand. The sensor apparatus can be used to approximate the properties of human mechanoreceptors and for detecting a variety of forces, including shear and dynamic forces.

Embodiments as disclosed herein, however, are not so limited. In other specific implementations, the spatial resolution, force sensitivity and/or response times may vary from the above-specific experimental embodiments, such as exhibiting a spatial resolution of 2 mm-10 mm, response time of 1 ms (or less)-5 ms, and/or a force sensitivity of 0.05N-200 kPa. The sensor apparatus can be used for tactile sensing of different kinds of dexterous activity (e.g., response, manipulation, and exploration) by meeting the above criteria and/or otherwise sensing normal and tangential forces and direction, as well as static and dynamic forces.

In specific embodiments, the sensor apparatus can be integrated into an electronic skin on a robot hand or a prosthetic, which can provide skin-like functionalities measuring three-axis static and dynamic force and its direction with a flexible mechanical property. The three-axis capacitive static and dynamic tactile sensor can distinguish forces in a three-dimensional axis and measure both static and dynamic forces from any surfaces of robot skin or prosthetic with flexible mechanical properties. The three-axis static and dynamic forces can be measured from any surfaces of robot skin or other types of surfaces. The advantage of the sensor apparatus is that design of an electrode and dielectric structure enables the sensor to distinguish all kinds of tactile forces such as normal and two-plane shear forces, static and dynamic forces. Moreover, a target technical specification, including force range and sensitivity of sensor circuitry, can be varied by the modification of the dimensions of dielectric microstructure and materials. The sensor apparatus or multiple sensor circuits can be used as a replacement for human mechanoreceptors, including use in robotics and/or prosthetic applications. For example, multiple sensor circuits can be placed on robot surfaces and used to give real-time force feedback to the robot. The dimensions of the sensor apparatus can be modified so that the range and resolution is tailored to meet the needs of different robotic (or prosthetic) applications.

The dielectric structure of the sensor apparatus can consist of circular pillars. The shape of these electrodes is that of a cross on an upper layer and four squares on a lower layer. However, embodiments are not so limited and the dielectric structures can include a variety of shapes. By designing the shape of electrodes and dielectric, the sensor apparatus can respond to multimodal external stimulation. The sensor apparatus can include a specific design, whereby multiple electrodes and polymer pillars detect force (normal/shear and static/dynamic) and direction simultaneously.

Turning now to the figures, FIG. 1 shows example sensor apparatus, consistent with embodiments of the present disclosure. As previously described, the sensor apparatus can include a capacitor coupled to sensor circuitry and used to detect both the type and magnitude of force applied, detect static and dynamic forces, and is flexible for application on surface that are not smooth, such as human skin. Furthermore, the sensor circuitry can detect a force's direction and vibration.

The sensor apparatus can include a capacitor formed of at least two substrates 102, 104. The substrates 102, 104 each include at least one electrode and are separated from one another by a dielectric layer 103. In specific embodiments, the substrates 102, 104 are formed of a flexible material and the electrodes can be formed on the flexible substrates. The first substrate 102 can include four electrodes (as further illustrated by FIG. 3A) and the second substrate 104 can include a cross-shaped electrode. The four electrodes can be square or rectangular shaped, although embodiments are not so limited.

The dielectric layer 103 can include a plurality of structures formed of a dielectric material, such as Polydimethylsiloxane (PDMS), although embodiments are not so limited. In specific embodiments, the dielectric layer 103 includes a plurality of circular pillars formed in a pattern and with gaps between the respective pillars.

The sensor circuitry is coupled to the capacitor formed of the at least two substrates 102, 104 and the dielectric layer 103. The sensor circuitry as further described herein detects normal and shear forces applied to the sensor apparatus based on changes in capacitance derived from changes in at least one of a distance between first and second electrodes and the overlapping area of the first and second electrodes.

Figure 2:
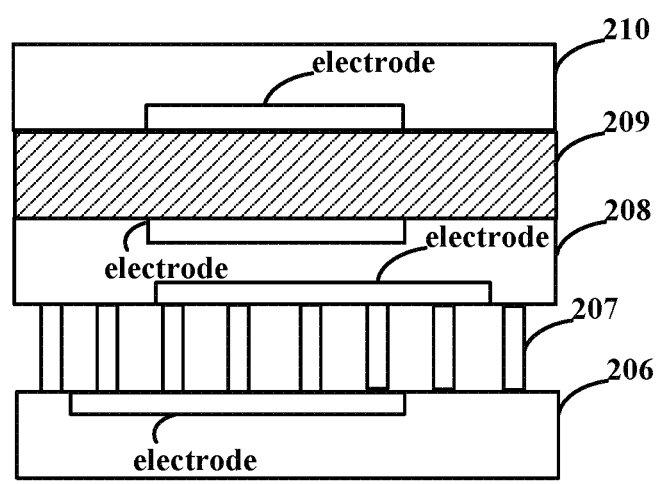
FIG. 2 shows an example sensor apparatus, consistent with embodiments of the present disclosure.

FIG. 2 shows example sensor apparatus, consistent with embodiments of the present disclosure. In some embodiments, the sensor apparatus can include one or more capacitors formed of at least two substrates 206, 208, 210. For example, the sensor apparatus includes three substrates 206, 208, 210, each substrate having at least one electrode, and being separated by dielectric layers 207, 209. The substrates are formed of a flexible material and the electrodes can be formed on the flexible substrates. The first substrate 206 can include one electrode (as further illustrated by FIG. 5A), the second substrate 208 can include two electrodes, and the third substrate 210 can include one electrode. The first substrate 206 is separated from the second substrate 208 by a first dielectric layer 207 and the second substrate 208 is separated from the third substrate 210 by a second dielectric layer 209. The electrodes of the second substrate 208, which is effectively sandwiched between the first substrate 206 and the third substrate 210 by the first and second dielectric layers 207, 209, can include a first electrode that is on a surface proximal to the first dielectric layer 207 and a second electrode on a surface proximal to the second dielectric layer 209. In specific embodiments, each of the electrodes can be rectangular shaped, however embodiments are not so limited.

The dielectric layers 207, 209 can include a plurality of structures formed of a dielectric material. In specific embodiments, the dielectric layers 207, 209 include a plurality of rectangular-shaped dielectric structures formed in a pattern and with gaps between the respective structures. The structures of the first dielectric layer 207 can extend in a pattern that is perpendicular to the structures of the second dielectric layer 209. For example, the length of the dielectric structures of the first dielectric layer 207 can extend in a z-direction (e.g., into the field of view) and the length of the dielectric structures of the second dielectric layer 209 can extend in a x-direction (e.g., left and right) of the field of view of the sensor circuitry. The first and second dielectric layers 207, 209 can effectively form a crisscross pattern of dielectric structures.

FIGS. 3A-3B show an example composition of a sensor apparatus as illustrated by FIG. 1, consistent with embodiments of the present disclosure. As previously described, the dielectric structure 312 of the sensor apparatus can consist of circular pillars. The shape of these electrodes is that of a cross on upper layer 313 and four squares or rectangles on lower layer 311. FIG. 3A illustrates the sensor apparatus from a top-down view and FIG. 3B illustrates a side view.

As further described herein, the magnitude of normal and shear static forces can be measured by measuring, monitoring and/or analyzing changes in capacitance derived from changes in distances between electrode pairs (e.g., the gap distance) and changes in overlapping areas of the electrode pairs, respectively, using sensor circuitry. The normal and shear forces can be distinguished based on the comparison of capacitance from each electrode pairs (e.g., formed by the electrodes of the lower layer 311 and the electrode of the upper layer 313). As used herein, normal forces includes or refers to pressure or compression forces on the sensor apparatus.

Figure 4A:
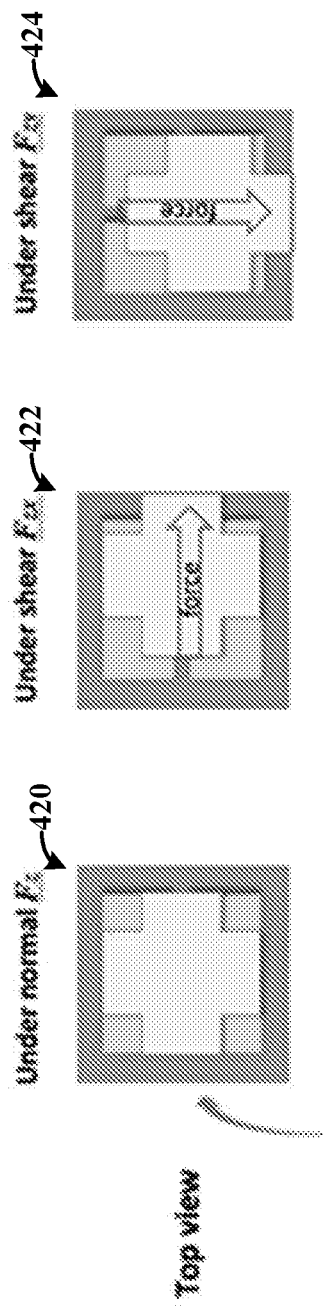
FIGS. 4A-4B show an example of sensor apparatus under different forces, consistent with embodiments of the present disclosure.
Figure 4B:
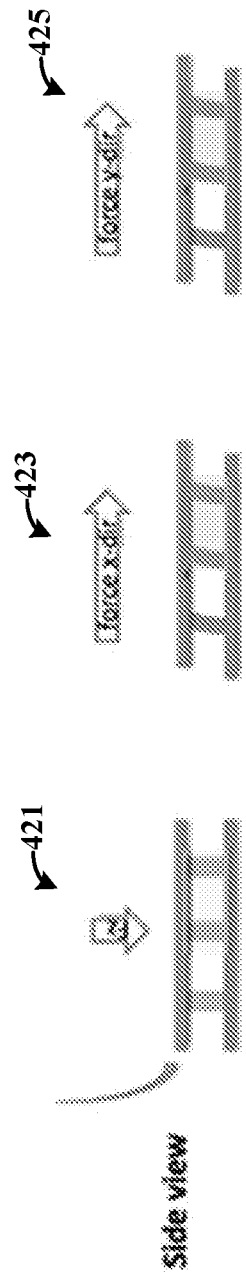

FIGS. 4A-4B show an example of a sensor apparatus under different forces, consistent with embodiments of the present disclosure. FIG. 4A illustrates the sensor circuitry from a top-down view and FIG. 4B illustrates a side view.

To measure a normal force, for example, when normal force is applied as illustrated by the top view 420 and the side view 421, the gap distance (e.g., distance between the electrode pairs and/or the electrode and the other/upper substrate) decreases (or otherwise changes) equally on the four electrodes of the lower (e.g., first) substrate, leading to equal changes in capacitance in all electrode pairs. The normal force can be classified by the average of capacitance of four electrode pairs by sensor circuitry. To distinguish between normal and shear forces, the direction of a shear force can be determined by comparing the different changes of capacitance in the four electrode pairs, as illustrated by the top view of 422 and 424. The overlapped areas on the four electrode pairs exhibit distinct changes in their capacitances according to the direction of force. For instance, when an x-directional shear force is applied from left to right side, as illustrated by the top view 422 and side view 423, the overlapped area, which is proportional to the capacitance, of left electrode pairs decrease, while the others increase in response to changes of overlapped area. These differing behaviors enable the sensor circuitry of the sensor apparatus to determine the direction of shear force. When a y-directional shear force is applied from top to bottom side, as illustrated by the top view 424 and the bottom view 425, the overlapped area and capacitance of top electrode pairs decrease, while the others increase. As would be appreciated by one of skill, left/right, top/bottom is with reference to the respective top views 420, 422, 424, and upper/lower is with reference to the side views 421, 423, 425.

The sensor circuitry can distinguish between torsion and diagonal shear force based on the design of the cross-shaped upper electrode. For example, the sensor circuitry can monitor the changes in capacitance exhibited by the cross-shaped electrode to distinguish between the torsion and diagonal shear forces. When torsion is applied, capacitance can change in quadratic since the overlapped area changes in triangles. On the other hand, diagonal shear force changes the overlapped area in squares (or rectangles) that changes the capacitance in linear.

The sensor circuitry can measure dynamic force by using the same transduction technology used for the static force by applying a high sampling rate (>500 Hz). In specific embodiments, the sensor circuitry includes at least one capacitance-to-digital converter (CDC) circuitry that connects at least some of the electrodes to an input channel of the CDC circuitry. The sensor circuitry can measure dynamic forces by measuring capacitance at a sample rate using the CDC circuitry and connected processing circuitry (e.g., microcontroller). To measure dynamic force by such a sampling rate, the sensor uses two CDC circuitry (Capacitance-to-Digital Converter chips) to connect the four electrode pairs to 2 of the 12 analog input channels of each chips, since a high sampling rate (>500 Hz) can be obtained from a lower number of capacitor inputs to the chip. The CDC chip consists of a sigma-delta-based CDC with 12 analog input channels and communicates with a microcontroller via an I2C bus, measuring capacitance in 0.3-1.2 kHz sampling rate, and cancelling noise from capacitors through active shield function. For more information on CDC chips and active shield function, reference may be made to AD7147, Analog, http://www.analog.com/media/en/technical-documentation/data-sheets/AD7147.pdf.

The fabrication process for the tactile sensor can address three primary components: electrode, dielectric layer, and bonding. The fabrication processing can include printing electrode pairs on one or more flexible substrates, building a dielectric layer on a first (or more) of the flexible substrates, bonding the dielectric layer of the first flexible substrate to a second flexible substrate, and optionally, repeating the process for additional layers to build a stack of electrode pairs. To print electrode patterns on flexible substrates, at first, metal deposition and laser ablation can be employed on flexible substrate. To build dielectric layers on these patterned electrodes, a mold is made with a SU8 Photolithography. PDMS can then be spin-cast onto the mold and cured under patterned electrode. This solidified PDMS can bond to a patterned electrode by chemical bond (e.g., chemical glue) and be peeled off from the mold. The last step is to bond it to another electrode by plasma treatment and, optionally, repeat the process to stack two electrode pairs. In various specific embodiments, the fabrication process can automate alignment of electrode pairs within the sensor circuitry.

Embodiments in accordance with the present disclosure can include various modification from that illustrated by FIG. 1, such as circuitry of sensor apparatus illustrated by FIG. 2. The modifications can include modification of the dimensions of dielectric (micro)structures can vary for target technical specification including force range and sensitivity of the sensor apparatus, materials can be substituted such as carbon nanomaterial, metal nanowires, and conductive polymers for electrode and any kind of polymers for dielectric, and the dielectric structure can be modified from circular pillar to plate or rectangular-shaped structure, such as for a one-pixel sensor.

FIGS. 5A-5B show an example composition of the sensor apparatus as illustrated by FIG. 2, consistent with embodiments of the present disclosure. As previously described, the dielectric layer of the sensor apparatus can consist of rectangular-shaped dielectric structures. One or more dielectric layers can separate different substrates having electrodes formed thereon. The shape of the electrodes can include rectangular shapes. FIG. 5A illustrates the sensor apparatus from a top-down view and FIG. 5B illustrates a side view.

As previously described by FIG. 2, the sensor apparatus can include capacitor having three substrates, each substrate having at least one electrode, and being separated by dielectric layers 532, 535. The substrates are formed of a flexible material and the electrodes can be formed on the flexible substrates. The first substrate can include an electrode 531 and a first dielectric layer 532 can be formed on the first substrate proximal to the electrode 531. The second substrate includes a first electrode 533 and a second electrode 534. The first and second electrodes 533, 534 of the second substrate are arranged to overlap and to be perpendicular to one another, thereby forming different channels (e.g., CH1 and CH2). The second substrate is separated from the first substrate via the first dielectric layer 532. As illustrated, the first electrode 533 of the second substrate is proximal to the first dielectric layer 532. A second dielectric layer 535 can be formed on the second substrate proximal to the second electrode 534 (or on the third substrate proximal to electrode 536). The second dielectric layer 535 separates the second substrate from a third substrate which includes an electrode 536. The first and second electrodes 533, 534 of the second substrate are effectively sandwiched between the first substrate and the third substrate by the first and second dielectric layers 532, 535. As may be appreciated by one of ordinary skill, the sensor apparatus illustrated by FIGS. 5A and 5B includes a stack of two electrode pairs. The first electrode pair is formed by the electrode 531 of the first substrate and first electrode 533 of the second substrate. The second electrode pair is formed by the second electrode 534 of the second substrate and the electrode 536 of the third substrate.

As illustrated by the top-view of FIG. 5A, the dielectric layers 532, 535 include a plurality of rectangular-shaped dielectric structures formed in a pattern and with gaps between the respective structures. The structures of the first dielectric layer 532 extend in a pattern that is perpendicular to the pattern of structures of the second dielectric layer 535. As illustrated, the length of the dielectric structures of the first dielectric layer 532 can extend in a z-direction (e.g., into the field of view) and the length of the dielectric structures of the second dielectric layer 535 can extend in a x-direction (e.g., left and right) of the field of view of the sensor circuitry.

FIGS. 6A-6C show an example of a sensor apparatus under different forces, consistent with embodiments of the present disclosure. FIG. 6A illustrates the sensor apparatus from a top-down view of the upper electrode pair (e.g., the second electrode pair), FIG. 4B illustrates a side view, and FIG. 6C illustrates a top view of the lower electrode pair (e.g., the first electrode pair). The sensor circuitry can be used to measure the magnitude of normal and shear static forces, similar to the above described sensor circuitry illustrated by FIGS. 4A-4B by analyzing changes in capacitance derived from changes in a gap distance and overlapping electrode area, respectively, of one or more of the electrode pairs in the stack. The normal and shear forces can be distinguished based on the comparison of capacitance from one or more of the electrode pairs.

To measure a normal force, for example, when normal force is applied as illustrated by the top view of the upper electrode pair 640, the top view of the lower electrode pair 642 and the side view 641, the gap distance decreases or otherwise changes for both the lower electrode pair and the upper electrode pair, leading to changes in capacitance in both electrode pairs. The normal force can be classified by the average of capacitance of the two electrode pairs by the sensor circuitry. To distinguish between normal and shear forces, the direction of a shear force can be determined by the sensor circuitry comparing the different changes of capacitance in the upper electrode pair and the lower electrode pair as illustrated by the top view of the upper and lower electrodes under different shear forces $F_{zx}$ and $F_{zy}$ (e.g., views 643, 644, 645, 646, 647, 648).

The overlapped areas on the two electrode pairs exhibit distinct changes in their capacitances according to the direction of force due to the arrangement of the first and second dielectric layers (e.g., the lengths of the rectangular dielectric structures extending in perpendicular directions with respect to dielectric structures of the other layer). For instance, when an x-directional shear force is applied from left to right side, as illustrated by the top views 643, 645 and side view 644, the overlapped area, which is proportional to the capacitance, of the lower electrode pair decreases, while the upper electrode pair remains the same or decreases a lower amount than the lower electrode pair. These differing behaviors enable the sensor circuitry to determine the direction of shear force. When a y-directional shear force is applied from top to bottom side, as illustrated by the top views 646, 648 and the bottom view 646, the overlapped area and capacitance of the upper electrode pair decreases, while the lower electrode pair remains the same or decreases a lower amount than the upper electrode pair.

The sensor circuitry can distinguish between torsion and diagonal shear force, in various embodiments. When torsion is applied, capacitance changes in the quadratic since the overlapped area changes in triangles. On the other hand, diagonal shear force changes the overlapped area between electrode pairs in rectangles that changes capacitance in linear. Similar to the x-axis or y-axis shear force illustrated in FIG. 4A, the changing shape of the overlapped area between electrode pairs is rectangular when diagonal shear force is applied to the sensor circuitry.

The sensor apparatus can measure dynamic force by using the same transduction technology used for the static force by applying a high sampling rate (>500 Hz). As previously described, to measure dynamic force by such a sampling rate, the sensor uses two CDC (Capacitance-to-Digital Converter) chips to connect the two electrode pairs to 2 of the 12 analog input channels of each chip In various specific embodiments, the sensor circuitry can be fabricated as described above, albeit repeating the process to form the stack of two electrode pairs.

In various embodiments, the sensing apparatus includes sensor circuitry that in contact with a human finger. The sensor apparatus is thin and flexible such that it can cover the curved finger surface. The sensor apparatus can be communication (wired or wireless) with processing circuitry, which is an example of sensor circuitry. The sensor apparatus can be connected to the processing circuitry, such as a laptop computer, by a printed circuit board. The processing circuitry can receive the signal data from the sensor apparatus and provide a graphical display of the resulting applied force on the sensor apparatus (e.g., the graph).

Various specific embodiments can include integrating the above-described sensor apparatus with robotics and prosthetics. For example, the sensor apparatus can be applied on target surfaces of robots for a robotic tactile sensing system as the mechanoreceptors of robot skin. On the robot skin or other prosthetic, flexible three-axis capacitive tactile sensor is freely applicable and indispensable for three distinct kinds of dexterous activities: response, manipulation, and exploration; which include the activity of response of detection and reaction to external agents, manipulation of contact location and force control, and exploration of surface texture and local features. In specific implementations, the sensor apparatus is formed as part of a robotic hand and is used to detect slip of an object being held or touched by the robotic hand. In related specific aspects, the sensor apparatus is formed as part of another apparatus (e.g., robotics, prosthetics and other implementations) having a plurality of different types of sensors including the sensor circuitry, pressure sensor circuitry, strain sensor circuitry, and/or temperature sensor circuitry, among other types of sensors.

Embodiments in accordance with the present disclosure are not limited to a sensor apparatus that is placed on an exterior surface (e.g., proximal to the environment) of robotics or prosthetics and can be directed to implants or other applications. In some specific embodiments, the sensor apparatus and/or another apparatus including the sensor apparatus can be implanted under an external surface of the skin of a user or other animal, i.e., is subdermal, and or below a surface of the robotics or prosthetic, similar to or including a passive radio frequency (RF) pet implant. For example, the sensor apparatus can be implanted a depth below the surface of the skin sufficient to be subcutaneous but not in muscle (e.g., within interstitial space of a user or other animal and/or prosthetic) and/or below a surface or the exterior surface of the robotics/prosthetic. In various embodiments, the implant is located below the surface of the skin, robotic and/or prosthetic sufficient for the implant including the sensor circuitry to communicate with external circuitry (e.g., to receive and output communications such as RF or other wireless signals).

Another aspect of the present disclosure, and in accordance with an example embodiment, uses one or more of the above types of sensor devices including a plurality of sensors, each including an impedance-based device having a compressible elastic dielectric material and circuit nodes separated by the dielectric material. Each sensor is configured to generate an output in response to impedance changes due to an amount of pressure applied to the dielectric material. Interconnecting circuits are respectively configured to couple the sensors and to provide an output indicative of pressure applied to the elastic dielectric at the respective sensors. For example, organic field-effect transistors can be manufactured with such a dielectric material, with the conductivity of the transistors (e.g., in their ON state) being related to the pressure. Accordingly, changes in pressure as amounting to either or both of increases and decreases in pressure are readily sensed.

The dielectric material can be implemented, or tuned, to suit different applications. In some implementations, spaces or pockets are formed within the dielectric material and/or between individual patterned regions of the dielectric material. The spaces/pockets may be filled with a fluid, gas, or other material exhibiting compression properties that are different than that of the dielectric material, and facilitate the elastic deformation and recovery of the dielectric material in response to applied pressure. For example, the spacing and/or air pockets can be tailored to enhance the dielectric material's ability to return to an original shape, after deformation. In certain implementations, the cross-sectional shape of the dielectric can be set to facilitate responsiveness/recovery to deformation, and to set the sensitivity of the shape to applied pressure. For instance, modifying the shape of the cross-section of a dielectric material can allow greater compression distance per unit force, thus increasing the sensitivity of the dielectric material to pressure.

Another approach to tuning characteristics of the dielectric material involves using different materials in different portions of a sensor and/or a combination of materials for a single sensor. For example, polydimethylsiloxane (PDMS), piezoelectric elastic materials, pyroelectric elastic polymers and ferroelectric elastic polymers can be patterned and used as discussed herein, alone or in combination with one another.

In addition, various portions of a sensor device can be tuned differently, with respect to material, shape and/or formation of spaces or air pockets. These approaches can be used to form sensors having a range of different sensing abilities. These sensing abilities can be tuned, for example, to a particular application or to a particular user. For example, by using air in the spaces/gaps, the displaced volume has a lower dielectric constant (=1.0) than an elastomer/dielectric (e.g., PDMS of ~3.0). Therefore, the increase in capacitance in the structured film arises from the reduction in the distance between the two electrode plates, and is enhanced further by the increase in dielectric constant.

Other aspects of the present disclosure are directed to a type of pressure-sensing apparatus that includes a circuit with an organic semiconductor substrate and/or other semiconductor material such as inorganic nanowires which are also flexible. The circuit with such deformable material provides sufficient material displacement in one or more directions (as in stretching and/or bending) for the indication of pressure. The circuit can include an elastic gate dielectric on the substrate configured to deform in response to pressure applied thereto, and a plurality of pressure sensors at different locations on the substrate. Each such sensor includes a FET-like (or an organic FET, OFET) arrangement with source and drain electrodes and a gate. For example, the source and drain electrodes can be coupled by a channel region that is in the substrate and adjacent the gate dielectric, and with the gate on the gate dielectric and configured to apply a bias to the channel region. The amount of the bias is responsive to deformation of the elastic gate dielectric in the channel region. The circuit is further configured with interconnecting conductors configured and arranged to couple a signal from each of the sensors, the signal being indicative of the deformation of the elastic gate dielectric via the applied bias.

Yet another aspect is directed to a type of apparatus or device having a three-dimensional sensitivity. The device comprises a transparent substrate having a plurality of sensors, with each sensor including electrodes electrically coupled by a compressible elastic dielectric material. The compressible elastic dielectric material compresses in response to pressure applied thereto, with each sensor being configured to exhibit an increased capacitance between the electrodes in response to the compression of the compressible elastic dielectric. The device can include a transparent conductive shielding material on the compressible elastic dielectric material, a light source configured to pass light corresponding to an image for viewing through the substrate and shielding material, and interconnecting circuits that respectively couple the sensors and provide a pressure-indicative output.

In some implementations, one or more of a material and shape of a dielectric elastomer is set to facilitate a response time to on and off pressure on the order of 10 ms or less, allowing for successive pressure sequences to be detected easily. For example, human finger actions are often physiologically limited to approximately 300 ms per action, such that response times faster than 300 ms facilitate the repeated application of pressure (e.g., taps).

In various embodiments, an elastomer/dielectric film as discussed herein is micro-patterned to mitigate visco-elastic creep and increases in relaxation times after compression, such as may relate to irreversible entanglement of polymer chains and the lack of a deformable surface. In connection with one or more such embodiments, it has been discovered that spaces (e.g., voids or gaps) between micro-structured portions of the film facilitate elastic deformation upon application of external pressure that, absent the spaces, may effect visco-elastic creep (e.g., a time-dependent increase in strain) in the film at its thickness. This facilitates the film's ability to store and release energy reversibly. Accordingly, various embodiments are directed to a sensor having an elastomer/dielectric film having separate regions patterned with respect to one another and a space therebetween, to facilitate reversible elastic deformation upon an applied pressure. This spacing and patterning (e.g., and the shape of the film) can be set to suit a particular application and an expected applied pressure, relative to the material used and mechanical properties thereof.

In certain embodiments, the elastic dielectric material for a sensor as discussed herein has a microstructure that connects circuit nodes of the sensor and a width dimension that is less than about 50 microns for certain implementations, less than about 30 microns for other implementations, and less than about 5 microns for certain other implementations. The dielectric layer may be a solid elastic dielectric layer for sensing the applied pressure, or may include a plurality of microstructures having gaps therebetween (e.g., filled with a non-solid material as discussed herein).

Other aspects of the present disclosure are directed toward apparatuses and methods involving at least one sensor implemented consistent with one or more of the above sensor types, in which the apparatus involves at least one of: a prosthetics device in which the sensor provides an output for operating the prosthetics device; a robotics device in which the sensor provides an output for facilitating automatic movement of the robotics device; and a medical device for insertion into a subject, in which the sensor provides an output for detecting pressure in the subject corresponding to pressure applied to one of the sensors.

Other embodiments are directed to electronic skin that can be used in artificial intelligence devices that come in to direct contact with humans, and in biomedical applications such as prosthetic skin. In order to mimic the tactile sensing properties of natural skin, large arrays of sensors as discussed herein are formed on a flexible and stretchable substrate, such as by using the biocompatible elastomer PDMS.

According to other aspects, in addition to displays, certain embodiments consistent with the instant disclosure use three-dimensional touch sensors on or as part of surfaces of input devices, which may include curved surfaces. Such devices include, for example, a computer mouse, rollable keyboards, or a gaming interface device. In some implementations, the sensors operate to replace mechanically-moving components such as buttons, and may be configured to provide an output corresponding to such components.

Another example embodiment is directed to the detection and prevention of excessive pressure on body tissue, such as during insertion of medical or surgical devices or cameras, using a flexible bio-neutral pressure sensor (e.g., near the tip of an instrument such as a camera head). This pressure sensitivity effectively gives feedback to the operator in a manner akin, for example, to sensing pressure on one's own skin.

In another embodiment, postoperative or post traumatic organ or tissue swelling is detected and monitored with a flexible bio-compatible pressure sensor patch using a pressure sensing device as discussed herein. The sensor patch may, for example, be further coupled to a small, bio-compatible radio frequency identification (RFID) device, which communicates pressure characteristics using wireless communications.

Power for the sensors as discussed herein can be obtained in a variety of manners. In some implementations, an external power supply or a battery are used. In other implementations, wireless power devices such as radio frequency devices that draw power from wireless signals are implemented with the sensors and used to power the sensors. In still other implementations, structuring is applied to piezoelectric films and a piezoelectric voltage that results from the exertion of pressure on the device powers the device.

Sensors as discussed herein may be implemented in a variety of applications. For example, one such application includes touch screen devices such as hand-held devices, televisions and computer devices, in which the sensor passes light (e.g., using a transparent elastomer material such as PDMS). Other applications are directed to force-sensing methods, such as resistive pressure sensors using conductive filler particles in elastomers, or quantum tunneling composites. Certain applications are directed to sensing changes in pressure, such as may be exhibited in a pressure vessel upon the development of a leak (e.g., a loss in pressure can be detected as a change in conductivity due to dielectric changes). Certain embodiments of the present disclosure are directed to sensing devices, wherein at least one sensor includes an elastic dielectric that is configured to exhibit an impedance change due to elastic capacitance (e.g., elastic capacitor as a discrete element or part of a capacitive circuit). Other applications are directed to medical applications, such as for sensing pressure within a body, or for prosthetic devices. Still other applications are directed to detecting pressure exerted on surfaces, such as by wind on a car or airplane body, and related deformations therein (e.g., to monitor for material stress), and can be used to understand frictional forces exerted by fluids (e.g., using a multi-sensor approach as discussed herein). Other applications involve sensing pressure in highly curved surfaces, such as in tubes the flow gasses and/or liquids, or in pressure vessels. Other applications are directed to portable, highly sensitive weighing scales, low fluid flow rate sensors, underwater touch sensors, pressure sensing systems for detecting driver fatigue by detecting low periods of low-pressure (or no) contact forces on curved surfaces of steering wheels during vehicle motion, and strain gauges (e.g., between movable joints).

Sensors as discussed in connection with one or more example embodiments can be manufactured using a variety of approaches, and can be implemented in a variety of applications. In one implementation, a sensor is manufactured on plastic substrates in a roll-to-roll process, which allows for high throughput and thus facilitates low commercialization costs. Accordingly, an elastomeric type roll can be manufactured with pressure-sensing electrodes in high-speed, facilitating the rapid manufacture of devices. Such sensors made on flexible substrates can be implemented with a variety of applications, such as curvilinear surface applications.

Cross-sections of example sensors and respective elastomer shapes, in accordance with various example embodiments of the present disclosure, can exhibit different shapes. Consider, for example, the respective sensors shown above having a common upper and lower region with differently-shaped elastomer (dielectric) materials therebetween being responsive in different manners to the application of a common pressure. The upper and lower portions can be separated by an elastomer material that compresses as would best seen along a generally vertical sidewall of the dielectric relative to its uncompressed shape. The elastomer dielectric material can have an inclined sidewall as exhibited in an uncompressed shape.

Modifying the shape of the elastomer cross-section can allow greater compression distance per unit force, thus increasing the sensitivity of the elastomer layer to pressure. In this context, various embodiments are directed to the implementation of elastomers having cross-sections that tune, or set, characteristics of a sensor in which the elastomers are used. Moreover, elastomers having different cross-sections can be used in a common device to set different pressure-sensing characteristics for different portions of the device. In various implementations, the cross-section of an elastomer is altered to set the sensitivity to pressure, and can be set to sense pressure of less than 1 kPa.

In some implementations, the elastomeric layer is shielded from the external environment by a conductive layer that keeps electric field lines within the elastomeric layer. Compressing the elastomer layer increases the effective dielectric constant of the material between electrodes. This increases the capacitance between the electrodes and thus, the pressure can be measured by the increase in capacitance.

Modifying the shape of the elastomer cross-section can also be implemented by in connection with a sensor device having a micro-structured polydimethylsiloxane (PDMS) film. At various stages of manufacture and in accordance with various example embodiments of the present disclosure, such a PDMS film can be manufactured to have tapered ends (e.g., with pointed/tipped ends pointing away from the planar portion of the film. In such a method of manufacture, a (e.g., Silicon) mold has a plurality of inverse (tapered) features. This is achieved by forming a PDMS film on mold (preformed to provide such features). A laminated film, such as indium tin oxide (ITO) coated poly(ethyleneterephthalate) (PET) substrate, is formed on the PDMS film, and the PDMS film is cured (e.g., cross-linked) under even pressure (e.g., at a temperature of about 70° C. for about three hours). The laminated film is then removed, with individual tapered portions of the PDMS film formed on the film, as shaped by the inverse features and set to suit the particular application with respect to compressibility.

The micro-structures in such PDMS film can be manufactured in a generally uniform (2-3% pitch fidelity) arrangement across the mold. These features can be replicated with high quality on very thin (e.g., <100 µm) and highly flexible plastic sheets. This approach can be used to ensure large-area compatibility of a pressure sensor, with respect to the tallest of the tapered PDMS features determining a contact plane. In addition, the tapered PDMS features can be set at a relatively small size (e.g., 3-6 µm or less in width, and less than 10 µm in height). In some implementations, a small glass plate is used to apply uniform pressure and improve lamination. Resulting film sensitivity can be achieved at about 0.55 kPa-1, with little to no hysteresis, and can detect weights of less than 20 mg and/or a pressure of about 3 Pa. Resulting film relaxation times can be achieved in the millisecond range.

In some FET/OFET embodiments, sensing circuitry is coupled across the source and drain electrodes, for detecting current therebetween and, accordingly, a degree of compression of the PDMS pillars. The sensing circuitry can be integrated with the device, or coupled as a separate device. Moreover, where a multitude of sensors are used (e.g., in a matrix), such as by implementing an array of sensors, the sensing circuitry may be coupled to two or more of these sensors to detect and/or process outputs thereof. In some implementations, the output processing circuitry provides a relatively simple output, such as may correspond to an actual measurement or response detected at $V_{SD}$, or may include processing circuitry that provides a more complex output characterizing the applied pressure, which may also be indicative of one or both of an amount of pressure and a location of the applied pressure.

The sensing devices may be manufactured in a variety of manners, such as discussed above, and may be arranged to suit particular applications. For example, the PDMS pillars may be formed in different shapes to set the sensitivity of the device, such as by tapering an end of the pillars as above. In some implementations, the source and drain electrodes are bottom contact gold electrodes and are formed on a highly n-doped silicon oxide wafer. The rubrene single crystal may, for example, be grown using physical vapor transport and laminated on top of the bottom contact gold electrodes. Such a crystal may, for example, be formed to exhibit a field-effect hole mobility on the order of 1 cm2/Vs. Other thin-film organic semiconductors with similar characteristics may also be similarly implemented.

A variety of different types of materials can be used to make sensors, in accordance with embodiments as discussed herein. In a particular example embodiment, a capacitive matrix-type pressure sensor is formed with all plastic components, apart from conductive or metal-type electrodes, by sandwiching a micro-structured dielectric film such as PDMS between two electrodes such as sheets of PET substrates (e.g., 25 µm thick) having conductors (e.g., vacuum-deposited aluminum metal lines (150 µm wide) that serve as address and data lines). The structure can be partitioned into sections (e.g., quadrants) of micro-structured PDMS film.

In some embodiments, a highly-stretchable material is used as a substrate to support patterned dielectric pillars to decrease signal spill-over from adjacent sensors (e.g., such that the translation of pressure upon a portion of the material/sensor to adjacent portions/sensors is mitigated or eliminated). For instance, such a material can be used in place of and/or with PET where implemented in various embodiments above.

In other embodiments, control circuitry is used to determine spillover based upon pressure sensed at different sensors within a matrix, using an algorithm-type input to determine an actual position of an applied pressure, relative to pressures sensed at different sensors. Such an approach can be implemented with sensing circuitry, when connected to a multitude of sensors. Moreover, such an approach can be used to interpolate the position of an applied pressure at or between sensors. Other embodiments are directed to the implementation of a matrix-type pressure sensor in a device that collects pressure information at multiple points. These approaches can be used to collect different types of inputs for a variety of devices.

In accordance with another example embodiment of the present disclosure, such an above-described sensor device includes an array of pressure-based sensors on a substrate. The array, by way of example, can have sixteen (or greater or fewer) sensors. Over the sensors is an array of dielectric regions, including a region 512 connected to a flexible substrate.

In operation, when pressure is applied to one such a flexible substrate, the dielectric regions compress at a region near the applied pressure, and the underlying sensors sense the applied pressure via a change in dielectric properties of the dielectric regions near the sensor. By processing outputs of the sensors at processing circuit, an indication of both a location and an amount of pressure applied to the flexible substrate can be provided. The sensors exhibit electrical changes based on the deformation and resulting changes in dielectric properties, thus providing an indication of the pressure. In this context, a three-dimensional pressure-sensing device is provided, sensing both position (e.g., in an x-y direction of a plane in which the sensors lie) and pressure (e.g., in a z direction into/about perpendicular to the aforesaid plane).

Also, such sensor devices may be implemented in accordance with an encapsulating substrate over an upper layer (or electrode), as a capacitive component and/or for a shielding effect as a dielectric layer. In addition, a conductive shielding portion or layer may be left floating, or set at ground potential.

Each such dielectric layer can have alternating regions of an elastomeric dielectric material and gap regions including a compressible substance such as air. The dielectric layer is formed over respective electrodes, including electrodes mounted on a substrate, which may form capacitors with the dielectric layer.

Another example embodiment and application is directed to one or more of the pressure sensors implemented to sense both vertical loads and shear force, consistent with the discussion above. Shear force information can be detected by grouping of oriented pressure sensor fields with either asymmetric microstructures or asymmetrically-arranged symmetric microstructures in groups (e.g., by orienting pressure sensor fields in North, West, South and East directions with groups of 2×2 superpixels). The response to vertical loads in the four sub-units of such a superpixel will be the same, thus any signal difference originates from in-plane (shear) stress exerted onto the sensor surfaces. The signal from the grouped sensors is calibrated and used to determine the sheer force vector and magnitude. Using this approach, pressure and shear forces can be detected and used, for example, to detect slip.

The above-disclosed embodiments, features and/or aspects can be used in connection with an intra-arterial/intra-venous pressure sensing application and device, in accordance with another example embodiment. Such a device can be used, for example, to detect pressure within a variety of different tissues, such as to produce surface maps of cell hardness. The device is configured for placement within an arterial or venial vessel wall, and includes a structured dielectric material, sense electrodes and counter electrodes located along the structured dielectric material, and a sensor substrate. The device may be placed using, for example, a catheter guide wire and an inflatable balloon, and be used for detecting pressure differences along the wall, such as may be present due to fatty deposits or diseased tissue as represented at, or can measure overall cell hardness. The sensors can be electrically coupled to the guide wire or a lead therewith, for providing a sensor output.

Various embodiments and features can be implemented and/or used in various combinations with the teachings disclosed herein and these include those aspects illustrated and/or described in the underlying Provisional Application (Ser. No. 62/530,667), entitled "Capacitive and Tactile Sensors and Related Sensing Methods," filed Jul. 10, 2017, to which benefit is claimed and which is fully incorporated herein by reference. For instance, embodiments herein and/or in the Provisional Application (including the Appendices A and B) may be combined in varying degrees (including wholly). Reference may also be made to the experimental teachings and underlying references provided in the underlying provisional application. Embodiments discussed in the slides are not intended, in any way, to be limiting to the overall technical disclosure, or to any part of the claimed invention unless specifically noted.

Also as should be apparent to the skilled artisan, unless otherwise indicated the various methods, structures, features shown/discussed in connection with the above embodiments and/or figures can be used in various combination and with a variety of technical applications.

Terms to exemplify orientation, such as top view/side view, before or after, upper/lower, left/right, top/bottom, above/below, and x-direction/y-direction/z-direction, may be used herein to refer to relative positions of elements as shown in the figures. It should be understood that the terminology is used for notational convenience only and that in actual use the disclosed structures may be oriented different from the orientation shown in the figures. Thus, the terms should not be construed in a limiting manner.

As examples, the Specification describes and/or illustrates aspects useful for implementing the claimed disclosure by way of various circuits or circuitry which may be illustrated as or using terms such as blocks, modules, device, system, unit, controller, and/or other circuit-type depictions. Such circuits or circuitry are used together with other elements (robotics, electronic devices, prosthetics, processing circuitry and the like) to exemplify how certain embodiments may be carried out in the form or structures, steps, functions, operations, activities, etc. For example, in certain of the above-discussed embodiments, one or more illustrated items in this context represent circuits (e.g., discrete logic circuitry or (semi)-programmable circuits) configured and arranged for implementing these operations/activities, as may be carried out in the approaches shown in the figures. In certain embodiments, such illustrated items represent one or more circuitry and/or processing circuitry (e.g., microcomputer or other CPU) which is understood to include memory circuitry that stores code (program to be executed as a set/sets of instructions) for performing a basic algorithm (e.g., inputting, counting signals having certain signal strength or amplitude, classifying the type of force including a magnitude and direction using capacitance values output by the sensor circuitry, sampling), and/or involving sliding window averaging, and/or a more complex process/algorithm as would be appreciated from known literature describing such specific-parameter sensing. Such processes/algorithms would be specifically implemented to perform the related steps, functions, operations, activities, as appropriate for the specific application. The Specification may also make reference to an adjective that does not connote any attribute of the structure ("first [type of structure]" and "second [type of structure]") in which case the adjective is merely used for English-language antecedence to differentiate one such similarly-named structure from another similarly-named structure (e.g., "first electrode . . . " is interpreted as "electrode configured to . . . ").

Based upon the above discussion and illustrations, those skilled in the art will readily recognize that various modifications and changes may be made to the various embodiments without strictly following the exemplary embodiments and applications illustrated and described herein. For example, methods as exemplified in the Figures may involve steps carried out in various orders, with one or more aspects of the embodiments herein retained, or may involve fewer or more steps. Such modifications do not depart from the true spirit and scope of various aspects of the disclosure, including aspects set forth in the claims.

What is claimed is:

1. A sensor apparatus comprising:
a capacitor including
a first substrate having a first electrode;
a second substrate having a second electrode that includes sections; and
a dielectric layer having a plurality of dielectric structures arranged in a pattern, the first and second electrode being separated by the dielectric layer and arranged with an overlapping area with respect to one another; and
sensor circuitry coupled to and operative with the capacitor and configured to detect diagonal shear forces applied to the sensor apparatus based on changes in capacitance indicated by monitoring the sections of the second electrode,
wherein the first substrate has four electrodes, including the first electrode, that are arranged in a pattern, and the second electrode of the second substrate is cross-shaped, and wherein the sensor circuitry is to distinguish between torsion and diagonal shear forces applied to the sensor apparatus by monitoring changes in the capacitance from the cross-shaped second electrode, wherein a torsion force results in capacitance changes in quadratic and the diagonal shear forces result in capacitance changes in linear.

2. The sensor apparatus of claim 1, wherein the first and second substrates are formed of a flexible material and configured to be placed on a curved surface.

3. The sensor apparatus of claim 1, further including processing circuitry in communication with the sensor circuitry, wherein the sensor circuitry is to define a magnitude of normal and shear forces applied to the sensor apparatus by measuring changes in capacitance derived from changes in a gap distance between the first electrode and the second electrode and provide signals indicative of the magnitude of the normal and shear forces to the processing circuitry.

4. The sensor apparatus of claim 1, wherein the sensor circuitry is to distinguish between shear and normal forces applied to the sensor apparatus by obtaining and comparing capacitance values from electrode pairs of the capacitor.

5. The sensor apparatus of claim 1, wherein each of the four electrodes of the first substrate has a portion that overlaps with an area of the second electrode of the second substrate.

6. The sensor apparatus of claim 1, wherein the plurality of dielectric structures includes a plurality of pillars.

7. The sensor apparatus of claim 1, wherein the dielectric structures include a plurality of gaps formed in a dielectric material that is arranged between the first and second substrates.

8. The sensor apparatus of claim 1, wherein the sensor circuitry includes capacitance-to-digital converter circuitry that connects the electrode of the first substrate to an input channel of the capacitance-to-digital converter circuitry, and the sensor circuitry is to measure capacitance at a sampling rate using the capacitance-to-digital converter circuitry and connected processing circuitry.

9. The sensor apparatus of claim 1, further including one or more electrodes used as a part of a transducer circuit and further including a passively or inductively powered circuit configured to provide power to at least the sensor circuitry.

10. The sensor apparatus of claim 1, further including a wireless communication circuit to communicate signals from the sensor circuitry.

11. A sensor apparatus comprising:
a capacitor including
a first substrate having a first electrode;
a second substrate having a second electrode; and
a dielectric layer having a plurality of dielectric structures arranged in a pattern, the dielectric layer being between the first and second substrates, and the first and second electrodes being separated by the dielectric layer and arranged with an overlapping area with respect to one another; and
sensor circuitry coupled to and operative with the capacitor to detect normal and shear forces applied to the sensor apparatus based on changes in capacitance derived from changes in at least one of a distance between the first and second electrodes and the overlapping area of the first and second electrodes, wherein the second substrate further includes a third electrode, and the capacitor further includes:
a third substrate having a fourth electrode, and
another dielectric layer between the second and third substrates.

12. The sensor apparatus of claim 11, wherein each of the dielectric layer between the first and second substrates and the other dielectric layer include a plurality of dielectric structures having gaps between, the dielectric structures of the dielectric layer between the first and second substrates being arranged perpendicularly with respect to the dielectric structures of the other dielectric layer.

13. The sensor apparatus of claim 11, further including processing circuitry in communication with the sensor circuitry, wherein the sensor circuitry is to define a magnitude of normal and shear forces applied to the sensor apparatus by measuring changes in capacitance derived from changes in a gap distance between the first electrode and the second electrode and provide signals indicative of the magnitude of the normal and shear forces to the processing circuitry.

14. The sensor apparatus of claim 11, wherein the sensor circuitry is to distinguish between shear and normal forces applied to the sensor apparatus by obtaining and comparing capacitance values from electrode pairs of the capacitor.

15. The sensor apparatus of claim 11, wherein the first substrate has four electrodes, including the first electrode, that are arranged in a pattern, and the second electrode is cross-shaped, wherein each of the four electrodes of the first substrate has a portion that overlaps with an area of the second electrode.

16. The sensor apparatus of claim 11, wherein the sensor circuitry is to distinguish between a diagonal shear force and at least one other type of force applied to the sensor apparatus by monitoring changes in the capacitance from sections of the second electrode.

17. The sensor apparatus of claim 16, wherein said at least one other type of force is a torsion force that results in capacitance changes in quadratic and wherein the diagonal shear force results in capacitance changes in linear.

18. A method of forming a sensing apparatus comprising:
printing electrode patterns on flexible substrates to form a capacitor having:
- a first flexible substrate having four electrodes arranged in a pattern ("the first electrode"); and
- a second flexible substrate having a second electrode that includes sections and is cross-shaped;

providing a dielectric layer having a plurality of dielectric structures arranged in a pattern on the first flexible substrate;

combining the dielectric layer and the second flexible substrate such that the first and second electrodes are separated by the dielectric layer and arranged with an overlapping area with respect to one another; and detecting diagonal shear forces applied to the sensing apparatus based on changes in capacitance indicated by monitoring the sections of the second electrode, wherein the sensing apparatus distinguishes between torsion and the diagonal shear forces applied to the sensing apparatus by monitoring changes in the capacitance from the cross-shaped second electrode, wherein a torsion force results in capacitance changes in quadratic and the diagonal shear forces result in capacitance changes in linear.

19. The method of claim 18, wherein combining the dielectric layer and the second flexible substrate includes forming the capacitor, and the method further includes to detect normal and shear forces applied to a sensor apparatus based on changes in capacitance derived from changes in at least one of a distance between the first and second electrodes and the overlapping area of the first and second electrodes.

20. The method of claim 18, wherein combining the dielectric layer and the second flexible substrate includes bonding the dielectric layer to the second flexible substrate.

21. The method of claim 18, wherein providing the dielectric layer includes curing dielectric material under a patterned electrode to bond the dielectric material to the patterned electrode.

22. The method of claim 18, further including providing the formed sensing apparatus as part of a robotic or prosthetic apparatus.

23. The method of claim 18, wherein the formed sensing apparatus is part of an apparatus having a plurality of different types of sensors at least one of which is from among the following: pressure sensor circuitry, strain sensor circuitry, and temperature sensor circuitry.

* * * * *